United States Patent
Colin et al.

(10) Patent No.: US 9,896,803 B2
(45) Date of Patent: Feb. 20, 2018

(54) FIBROUS SHEET THAT DISINTEGRATES IN WATER, PROCESS FOR MANUFACTURING SAID FIBROUS SHEET, CORE CONSISTING OF STRIPS OF SAID FIBROUS SHEET

(71) Applicant: SCA TISSUE FRANCE, Saint-Ouen (FR)

(72) Inventors: Philippe Colin, Ingersheim (FR); Jean-Claude Dozzi, Soultzbah-les-bains (FR); Pierre Probst, Ammerschwihr (FR); Véronique Wiss, Hessenheim (FR); Rémy Ruppel, Durrenentzen (FR)

(73) Assignee: SCA TISSUE FRANCE, Saint-Ouen (FR)

( * ) Notice: Subject to any disclaimer, the term of this patent is extended or adjusted under 35 U.S.C. 154(b) by 770 days.

(21) Appl. No.: 14/471,321

(22) Filed: Aug. 28, 2014

(65) Prior Publication Data

US 2014/0367060 A1    Dec. 18, 2014

Related U.S. Application Data

(62) Division of application No. 13/264,114, filed as application No. PCT/IB2010/002190 on Jun. 11, 2010, now Pat. No. 9,039,651.

(30) Foreign Application Priority Data

Aug. 3, 2009 (FR) .................................... 09 03827

(51) Int. Cl.
| | | |
|---|---|---|
| D21H 17/28 | (2006.01) | |
| D21H 27/30 | (2006.01) | |
| A47K 10/22 | (2006.01) | |
| A61F 13/26 | (2006.01) | |
| D21H 19/54 | (2006.01) | |
| D21H 25/04 | (2006.01) | |
| D21H 27/00 | (2006.01) | |

(52) U.S. Cl.
CPC .............. D21H 17/28 (2013.01); A47K 10/22 (2013.01); A61F 13/266 (2013.01); D21H 27/30 (2013.01); D21H 19/54 (2013.01); D21H 25/04 (2013.01); D21H 27/002 (2013.01)

(58) Field of Classification Search
CPC ........ D21H 17/28; D21H 19/54; D21H 25/04; D21H 27/30; D21H 27/002; A61F 13/266; A47K 10/22
USPC ...................................................... 162/123
See application file for complete search history.

(56) References Cited

U.S. PATENT DOCUMENTS

| 1,761,111 | A | 6/1930 | Doty |
|---|---|---|---|
| 1,824,421 | A | 9/1931 | Allen |
| 3,580,253 | A | 5/1971 | Bernardin |
| 4,473,368 | A | 9/1984 | Meyer |
| 5,242,545 | A | 9/1993 | Bradway et al. |
| 5,576,364 | A | 11/1996 | Isaac et al. |
| 6,166,857 | A | 1/2001 | Andersen et al. |
| 6,200,404 | B1 | 3/2001 | Andersen et al. |
| 6,818,101 | B2 | 11/2004 | Vinson et al. |
| 7,951,440 | B2 | 5/2011 | Butler, III |
| 8,075,699 | B2 | 12/2011 | Butler, III |
| 2002/0084045 | A1 | 7/2002 | Collias et al. |
| 2002/0096287 | A1 | 7/2002 | Jewell et al. |
| 2006/0037724 | A1 | 2/2006 | Akai et al. |
| 2007/0048474 | A1 | 3/2007 | Butler et al. |
| 2009/0075001 | A1 | 3/2009 | O'Neill |
| 2011/0287273 | A1 | 11/2011 | Weisang et al. |
| 2011/0305855 | A1 | 12/2011 | Graff et al. |
| 2012/0089075 | A1 | 4/2012 | Colin et al. |

FOREIGN PATENT DOCUMENTS

| DE | 4431755 A1 | 3/1996 |
|---|---|---|
| EP | 0372388 A2 | 6/1990 |
| EP | 0415385 A1 | 3/1991 |
| EP | 0438672 A1 | 7/1991 |
| EP | 0639381 A1 | 2/1995 |
| EP | 1459876 A2 | 9/2004 |
| EP | 1630288 A1 | 3/2006 |
| GB | 691552 A | 5/1953 |
| GB | 22002750 A | 10/1988 |

(Continued)

OTHER PUBLICATIONS

PCT International Search Report dated Jul. 7, 2010 for International Application No. PCT/EP2009/067270; International Filing date: Dec. 16, 2009, 6 pages.
PCT Written Opinion dated Jun. 7, 2010 for International Application No. PCT/EP2009/067270; International Filing date: Dec. 16, 2009, 11 pgs.
English Translation of the Written Opinion of the International Searching Authority Issued in PCT/IB2010/002165 dated May 19, 2011.
PCT International Search Report for International Application No. PCT/IB2010/002165; International Filing date: Jun. 11, 2010; dated Feb. 25, 2011, 4 pages.

(Continued)

*Primary Examiner* — Mark Halpern
(74) *Attorney, Agent, or Firm* — Drinker Biddle & Reath LLP (57) ABSTRACT

A fibrous sheet having a basis weight of between 20 and 1000 g/m² that disintegrates in water, has 10% to 70% starch on the basis of the total weight of the dry fibrous sheet. The disintegration time in water, measured in accordance with standard NF Q34-020 applied to a specimen of the sheet of 9×8 cm², is less than 50 seconds. A loss of strength of the sheet measured in accordance with a defined table test corresponds to a loss of strength of a specimen of said sheet forming an angle of at least 85° after having being wetted with water for a duration of 6 seconds, and/or a residual wet strength of the sheet relative to its dry strength, as measured according to a defined ring crush test, is less than 1%. The fibrous sheet may be used for the manufacture of a water disintegrable core in a roll of tissue paper.

6 Claims, 2 Drawing Sheets

(56) References Cited

FOREIGN PATENT DOCUMENTS

| GB | 2401870 A | 11/2004 |
|---|---|---|
| JP | S62211029 A | 9/1987 |
| JP | 2005089911 A | 4/2005 |
| WO | WO-0006462 A1 | 2/2000 |
| WO | WO-00/44982 A1 | 8/2000 |
| WO | WO-0121121 A1 | 3/2001 |
| WO | WO-0174939 A1 | 10/2001 |
| WO | WO-0247998 A1 | 6/2002 |

OTHER PUBLICATIONS

PCT International Search Report and Written Opinon for the International Application No. PCT/EP2009/067324 dated Apr. 19, 2010.
English Translation of the Written Opinion of the International Searching Authority Issued in PCT/IB2010/002190 dated Feb. 24, 2011.
PCT International Search Report for International Application No. PCT/IB/2010/002190, International Filing date: Jun. 11, 2010; dated Feb. 24, 2011, 3 pages.
France Search Report for Application No. 09 03827; filing date Aug. 3, 2009; Completion date, Feb. 25, 2010; 2 pages.
English Translation of the Written Opinion of the International Searching Authority Issued in PCT/IB/2010/002165 dated May 19, 2011.
PCT International Search Report for International Application No. PCT/IB/2010/002165, International Filing date: Jun. 11, 2010; dated Feb. 25, 2011, 4 pages.
PCT International Search Report and Written Opinion for the International Application No. PCT/EP2009/067324, dated Apr. 19, 2010.

FIBROUS SHEET THAT DISINTEGRATES IN WATER, PROCESS FOR MANUFACTURING SAID FIBROUS SHEET, CORE CONSISTING OF STRIPS OF SAID FIBROUS SHEET

This is a Divisional of copending application Ser. No. 13/264,114, filed Dec. 13, 2011, which is a PCT National Stage of PCT/IB2010/002190 filed Jun. 11, 2010, which claims priority to France Application No. 09 03827 filed Aug. 3, 2009, which are herein incorporated by reference in their entirety.

The present invention relates to a disintegrable fibrous sheet, its manufacture, as well as a core having such a fibrous sheet, a toilet paper roll having such a core and a tampon applicator having such a fibrous sheet.

DEFINITIONS

For the sake of clarity, the following definitions of facts known to a person skilled in the art shall be presented:

The term "disintegration" corresponds to the definition of total disintegration given in NF Q34-020 standard, i.e. there are no more important pieces and the dispersion of the pieces is homogeneous.

The term "wet papermaking process" means a method of manufacturing a fibrous sheet while using a wet-end sheet forming. More precisely, this method comprises a pulp or furnish preparation section, a wet forming section, a press section for removing water and a dry section.

The furnish preparation section consists in mixing the different components including fibres, fillers and additives with water for providing the aqueous suspension or furnish. The wet forming section can be implemented on a flat table such as a Fourdrinier table or any other cylindrical forming apparatus. The headbox can be provided with one jet or multiple jets distributor. The press section consists in removing water by mechanically pressing the web. The dry section can comprise a conventional dryer such as drying drums, Yankee dryer, through air drying cylinders, infrared dryers, and the like to remove water by heat exchange. Then the thus obtained sheet is wounded on a reel as a final product.

The term "cellulosic", "cellulosic fibre" and the like is meant to include any fibre incorporating cellulose as a major constituent.

The term "Papermaking fibres" means cellulosic fibres and includes virgin pulps or recycle (secondary) cellulosic fibres or fibre mixtures comprising reconstituted cellulosic fibres. Cellulosic fibres suitable for making the fibrous sheet of this invention include: non wood fibres, such as cotton fibres or cotton derivatives, abaca, kenaf, sabai grass, flax, esparto grass, straw, jute hemp, bagasse, milkweed floss fibres, and pineapple leaf fibres; and wood fibres such as those obtained from deciduous and coniferous trees, including softwood fibres, such as Northern and Southern softwood Kraft fibres; hardwood fibres, such as Eucalyptus, maple, birch, aspen, or the like. Papermaking fibres used in connection with the invention include naturally occurring pulp-derived fibres as well as reconstituted cellulosic fibres such as lyocell or rayon. Pulp-derived fibres are liberated from their source material by any one of a number of pulping processes familiar to one experienced in the art including sulfate, sulfite, polysulfide, soda pulping, etc. The pulp can be bleached if desired by chemical means including the use of chlorine, chlorine dioxide, oxygen, alkaline peroxide and so forth. Naturally occurring pulp-derived fibres are referred to herein simply as "pulp-derived" papermaking fibres. The products of the present invention may comprise a blend of conventional fibres (whether derived from virgin pulp or recycle sources) and high coarseness lignin-rich tubular fibres, such as bleached chemical thermomechanical pulp (BCTMP). Pulp-derived fibres thus also include high yield fibres such as BCTMP as well as thermomechanical pulp (TMP), chemithermomechanical pulp (CTMP) and alkaline peroxide mechanical pulp (APMP). "Furnishes" and like terminology refer to aqueous compositions including papermaking fibres, optionally wet strength resins, de-bonders and the like for making paper products Kraft softwood fibre is low yield fibre made by the well known Kraft (sulfate) pulping process from coniferous material and includes Northern and Southern softwood Kraft fibre, Douglas fir Kraft fibre and so forth. Kraft softwood fibres generally have a lignin content of less than 5 percent by weight, a length weighted average fibre length of greater than 2 mm, as well as an arithmetic average fibre length of greater than 0.6 mm.

Kraft hardwood fibre is made by the Kraft process from hardwood sources, i.e., Eucalyptus, and also has generally a lignin content of less than 5 percent by weight. Kraft hardwood fibres are shorter than Softwood fibres, typically having a length weighted average fibre length of less than 1.2 mm and an arithmetic average length of less than 0.5 mm or less than 0.4 mm.

Recycle fibre may be added to the furnish in any amount. While any suitable recycle fibre may be used, recycle fibre with relatively low levels of groundwood is preferred in many cases, for example, recycle fibre with less than 15% by weight lignin content, or less than 10% by weight lignin content may be preferred depending on the furnish mixture employed and the application.

In addition, the fibrous sheet according to the invention can also contain non-cellulosic fibres such as synthetic polymer fibres and the like. This terminology refers to fibre made from synthetic polymers such as polyesters, nylons and polyolefins and so forth. Polyesters are generally obtained by known polymerization techniques from aliphatic or aromatic dicarboxylic acids with saturated aliphatic or aromatic diols.

BACKGROUND OF THE INVENTION

Paper for sanitary or domestic use, such as toilet paper, paper towels or wipes, are in certain cases packaged in the form of rolls on a core.

The core is a cylinder, generally made of cardboard, which is discarded after the paper of the roll has been consumed. The core fulfils several functions:

It serves as support on which the paper sheet is wound during manufacture of the roll. In general, the rolls are manufactured from a very wide master sheet, also called jumbo roll, which is wound around a tube of corresponding length, and the roll obtained is sawn into individual rolls of the desired width;

it keeps the central hole open by withstanding the internal stresses of the roll and preventing the internal turns of the winding from collapsing; and it keeps the roll in shape by withstanding the crushing forces along its axis or the transverse forces to which the roll is subjected during transportation or during the various handling operations before it is used.

The core is generally obtained by the helical winding and bonding of one or more flat cardboard strips around a cylindrical former.

Flat cardboard is an inexpensive material, which may be made from recycled fibres. It is also light and its mechanical strength is sufficient for this use.

However, it has the drawback of not being able to be reused or of being rarely utilized in another form after the roll has been consumed and of becoming a waste product.

In the case of toilet paper, it is not recommended to dispose of the standard core by attempting to discharge it with the wastewater as, although composed predominantly of paper making fibres, in particular cellulosic fibres, it disintegrates slowly on contact with water and generally fails to be removed from the toilet bowl, or else it forms a plug and obstructs toilet drain lines before it can be flushed away by the flow.

The Applicant set itself the objective of producing a core for a roll that can be easily discharged with the wastewater of a domestic sanitary facility.

More particularly:

The core must quickly disintegrate on contact with water;

the material must disintegrate in water at a rate sufficient for it to be discharged before forming a plug; the rate at which it disintegrates must be comparable, for the same mass, to that of the tissue paper of which the rolls are generally composed;

the core must have a crush resistance, both in the radial direction and the axial direction, of the same order of magnitude as that of the cardboard that it is intended to replace;

The core must be as easy and as simple to produce as conventional cardboard cores; and The core must be manufactured with renewable materials; it should have no negative impact in paper recycling processes nor water treatment plants processes as well.

PRIOR ART

Products in sheet or other form, produced with papermaking fibres, in particular cellulosic fibres, and starch are generally known.

EP 415 385 describes the manufacture of a paper sheet with incorporation of a water-insoluble modified starch, a starch urea phosphate, which is gelatinized during drying, the gelatinization temperature of said starch being relatively low, namely between 35° C. and 55° C. The objective is to improve the dry strength of the sheet obtained and avoid filling of the wire in the paper machine during the manufacturing process.

EP 1 630 288 describes an embossed and impregnated paper sheet, disintegrable in water, intended for use as a cleaning sheet as a wet wipe. It contains a water-soluble binder, such as a polysaccharide or a synthetic polymer, and an aqueous agent associated with an agent that makes the water-soluble binder temporarily insoluble. According to the examples given, the sheet disintegrates in 30 to 40 seconds, the disintegration speed being measured using the standard method referenced JIS P4501 applied to a square specimen of paper sheet weighing 0.3 g.

U.S. Pat. No. 6,168,857 describes a biodegradable product, for example taking the form of a sheet. It consists of a starch matrix reinforced with papermaking fibres or the like and is obtained by moulding. The prior mixture consists of at least ungelatinized starch, fibres and water. The product is obtained by moulding the mixture. A polymer such as cellulosic ether is added so as to form a film on the surface, which prevents sticking during manufacture of the product.

SUBJECT OF THE INVENTION

The qualities of the core are at least partly dependent on the constituent fibrous sheet.

Fibrous Sheet

The invention refers to a fibrous sheet having a basis weight of between 20 and 1000 g/m$^2$ that disintegrates in water, comprising 10% to 70% starch on the basis of the total weight of the dry fibrous sheet, a. the disintegration time in water, measured in accordance with the NF Q34-020 standard applied to a specimen of the sheet of 9×8 cm$^2$, is less than 50 seconds, preferably less than 35 seconds, and more particularly less than 15 seconds, b. of which the loss of strength measured in accordance with the table test as reported in the specification corresponds to the loss of strength of a specimen of said sheet forming an angle of at least 85°, preferably between 88° and 90°, after having being wetted with water for a duration of 6 seconds.

The invention also refers to a fibrous sheet having a basis weight of between 20 and 1000 g/m$^2$ that disintegrates in water, comprising 10% to 70% starch on the basis of the total weight of the dry fibrous sheet, a. the disintegration time in water, measured in accordance with the NF Q34-020 standard applied to a specimen of the sheet of 9×8 cm$^s$, is less than 50 seconds, preferably less than 35 seconds and more particularly less than 15 seconds, b. the residual wet strength of which relative to its dry strength, as measured according to the ring crush test described in the specification, is less than 1%.

The invention also relates to a fibrous sheet having a basis weight of between 20 and 1000 g/m$^2$ that disintegrates in water, comprising 10% to 70% starch on the basis of the total weight of the dry fibrous sheet, a. the disintegration time in water, measured in accordance with the NF Q34-020 standard applied to a specimen of the sheet of 9×8 cm$^2$, is less than 50 seconds, preferably less than 35 seconds and more particularly less than 15 seconds, b. the residual wet strength of which relative to its dry strength, as measured according to the ring crush test described in the specification, is less than 1%.

The invention also relates to a fibrous sheet having a basis weight of between 20 and 1000 g/m$^2$ that disintegrates in water in less than 120 seconds comprising 10% to 70% starch on the basis of the total weight of the dry fibrous sheet, a. of which the loss of strength measured according to the table test as reported in the specification corresponds to the loss of strength of a specimen of said sheet forming an angle of at least 85°, preferably between 88° and 90°, after having being wetted with water for a duration of 6 seconds, b. the residual wet strength of which relative to its dry strength, as measured according to the ring crush test described in the specification, is less than 1%.

The invention also relates to a fibrous sheet having a basis weight of between 20 and 1000 g/m$^2$ that disintegrates in water comprising, 10% to 70% starch on the basis of the total weight of the dry fibrous sheet, a. the disintegration time in water, measured in accordance with the NF Q34-020 standard applied to a specimen of the sheet of 9×8 cm$^2$, is less than 50 seconds, preferably less than 35 seconds and more particularly less than 15 seconds, b. of which the loss of strength measured according to the table test as reported in the specification corresponds to the loss of strength of a specimen of said sheet forming an angle of at least 85°, preferably between 88° and 90°, after having been wetted with water for a duration of 6 seconds, c. the residual wet strength of which relative to its dry strength, as measured according to the ring crush test described in the specification, is less than 1%.

In a preferred embodiment, the sheet has at least one of the following features:

It contains 15 to 40% starch on the basis of the total weight of the dry fibrous sheet.

The basis weight is between 100 and 600 $g/m^2$, preferably between 130 and 400 $g/m^2$.

It contains at least 30% of papermaking fibres.

The papermaking fibres are cellulosic fibres and contain virgin fibres or recycled fibres or a combination thereof.

The fibrous sheet contains additives for providing a function additional to that of the starch, such as disinfectants, cleaning agents, dyes or fragrances.

Starch is substantially uniformly distributed through the thickness of the fibrous sheet. The term "substantially uniform" means that the starch is distributed right through the thickness of the sheet so as to provide most of the links between the fibres, and is also present on the external surfaces of the sheet.

The invention further relates to a process for manufacturing a fibrous sheet comprising at least 30% of papermaking fibres, that disintegrates in water in less than 120 seconds, according to one of the aforementioned aspects of the invention relating to the fibrous sheet, comprising a step of preparing a pulp by suspending fibres in water, a step of forming the fibrous sheet from the pulp and a drying step, characterized in that it further comprises the steps of adding to the fibrous sheet, before the drying step, a starch which is not soluble in water at the temperature at which it is incorporated, and drying the fibrous sheet containing the starch at a temperature high enough to gelatinize at least some of the starch.

According to an other aspect of the invention, a process for manufacturing a fibrous sheet that disintegrates in less than 120 seconds in water according to one of the aforementioned aspects of the invention relating to the fibrous sheet, is characterized in that it comprises the steps of suspending fibres in water, forming at least a first fibrous ply and a second fibrous ply with said fibres, depositing a starch on the second fibrous ply, depositing the first fibrous ply on the second one, joining the two plies together as a fibrous sheet and drying the fibrous sheet In an advantageous manner, a core consists of a helical winding of one or more strips, wherein the strip(s) are made of a fibrous sheet according to one of the aforementioned aspects of the invention relating to the fibrous sheet.

Furthermore, according to an other aspect of the invention, a toilet paper roll comprises a core with the aforementioned features.

Finally, according to a still further aspect of the invention, there is provided a tampon applicator having a fibrous sheet according to one of the aforementioned aspects of the invention relating to the fibrous sheet.

Further advantageous aspects of the invention can be seen from the set of claims and the detailed description.

In any aspect of the invention, the structure of the fibrous sheet can be designed advantageously such that a pre-defined and desired disintegration combined with pre-defined and desired mechanical properties such as residual strength properties of the fibrous sheet and the products made out of it, namely toilet paper rolls and tampon applicators, are achieved. In an advantageous manner the strength of a fibrous sheet according to the invention is comparable to that of cardboard.

In the following, two advantageous manufacturing processes according to the invention shall be presented, the first one referring to the application of a starch being insoluble in water (hereinafter referred to as "process I"), the second one referring to the application of a starch being soluble in water (hereinafter referred to as "process II").

Process I for Manufacturing a Sheet with a Starch Insoluble in Cold Water.

The process for manufacturing a fibrous sheet comprising at least 30% of papermaking fibres that can disintegrate in less than 120 seconds in water comprises a step of preparing a pulp by suspending said fibres in water, a step of forming the sheet from said pulp and a drying step. This process is characterized in that it includes the addition, before said drying step, of a starch which is not soluble in water at the temperature at which it is incorporated, and the drying of the sheet containing the starch at a temperature high enough to gelatinize at least some of the starch. The purpose is to make the starch soluble in water so that the sheet is disintegrable.

The expression "water-insoluble starch" is understood to mean a starch which, when cold, mixed with water and stirred, essentially forms a suspension. In other words, the starch grains or particles remain predominantly suspended in water. When the stirring is stopped, the starch particles precipitate. The temperature at which it is incorporated is below the gelatinization temperature of the starch.

From a minimum of basis weight of the sheet, i.e. 150 $g/m^2$, most of the starch particles are thus retained by the fibrous mat and are therefore not entrained with the white water during dewatering on the forming table or in the presses. The degree of starch retention is therefore high.

Starch comprises natural products of plant origin, such as wheat, maize, potato, rice, tapioca or sorghum starches, and other starches, composed of polymers or polysaccharides of high molecular weight. The plant matter is treated by grinding-steeping and centrifugation in order to extract the starch. Native starch corresponds to the product extracted without molecular modification. Native starch is insoluble in water—it behaves as filler. The starch is mixed, with stirring, into excess water so as to form a starch suspension. When the temperature of the starch suspension rises, water penetrates into the starch particles, these starch particles swell and the suspension is converted into a colloidal solution which thickens, gelatinizes and becomes viscous. The gelatinization temperature depends on the plant: maize 60-72° C.; wheat 60-65° C.; tapioca 52-64° C.; potato 58-66° C. By continuing to heat, the particles burst and the macromolecules constituting the starch emerge from the particles and dissolve in water. The presence of water in sufficient amounts is essential for this gelatinization and dissolution of the starch.

The preferred starches that can be used in the process, in so far as they are insoluble in water, may thus comprise products derived from natural starch, which are converted by a physical, chemical or physico-chemical treatment or by a biological treatment, for example an enzyme treatment, and derived or modified starches such as cationic, anionic, amphoteric, non-ionic or crosslinked starches and products resulting from starch hydrolysis, such as maltodextrins. These starches are termed modified starches, while still keeping the property of being insoluble in water.

Preferably, a tuber starch is used, such as potato starch, since the particles are relatively coarser than those of other starches, for example maize starch, and has a higher retention in the sheet.

A preferred starch is an anionic modified potato starch, such as a starch marketed under the name Perfectacote A35 from Avebe, or a non ionic starch named Stackote 6 form National Starch. Preferred starches present a substitution grade of 0.01 to 0.07 wherein the substituted groups are carboxylic groups. These starches have a low viscosity at the gelatinization temperature (52° C. for Perfectacote) that remains very stable with the time. For the present use this property is favourable to a good distribution within the fibrous sheet.

Preferably, the aim is to gelatinize all the starch present in the sheet and provide a starch distribution through the whole thickness of the sheet.

The process according to the invention advantageously includes a step of pressing the sheet before the drying step.

The water-insoluble starch is incorporated into the process water, which is at a temperature generally below 50° C.

The water-insoluble starch is advantageously incorporated into the pulp upstream of the forming table. The starch suspension may thus be uniformly mixed with the pulp fibres.

It may also be envisioned, although this is not optimal, to incorporate the water-insoluble starch when the sheet is on the forming wire, especially by spraying it onto the sheet or by any other conventional means of application.

The water-insoluble starch is supplied in an amount sufficient to give the sheet the above-mentioned properties.

According to another feature, the sheet is dried with the temperature being progressively raised so as to reach complete gelatinization of the starch and to make it soluble. By progressively raising the temperature, it is possible to control the amount of water present in the sheet at the gelatinization temperature and to maintain a sufficient amount of water for making all the particles burst.

The invention does not exclude the possibility of adding an additional step consisting in depositing a certain amount of starch by couching in the drying section so as to give the paper sheet a particular property, provided that this additional layer does not impair the disintegrability of the sheet.

Process II for Manufacturing a Sheet with a Water-Soluble or Water Insoluble Starch The process for manufacturing a fibrous sheet comprising at least 30% of papermaking fibres that can disintegrate in less than 120 s. in water is characterized in that it consists in forming at least a first ply and a second ply of fibres by wet processing, in depositing the starch on the second fibrous ply, in depositing the first fibrous ply on the second fibrous ply, in joining the two plies to form a sheet and in drying said sheet.

The number of plies is not limited to two—the sheet may comprise at least three plies, for example up to about ten plies. The starch can be deposited between the plies after they have been formed but this is not mandatory.

The starch is supplied in an amount sufficient to give the sheet the above properties.

When water-soluble the starch is chosen so that its rate of dissolution is appropriate with the amount of water present in the paper fibre ply formed by wet processing. It is thus capable of giving the sheet both dry strength and solubility in water.

Usually, water-soluble starches are modified starches including maltodextrins compounds. Some examples of such starches are AVEDEX (dextrinized potato starch) from AVEBE, CARGILL MD01904 (maltodextrins) from CARGILL.

When water insoluble the starch s chosen as in process I.

According to a preferred embodiment, the starch is supplied dry, in the form of a powder or in the form of a sheet or a film. This embodiment is advantageous in so far as the starch is activated by the water present in the fibrous plies without supplying additional water.

According to another feature, the sheet is pressed, before drying or calendered after drying, in order to obtain a sheet after drying with a density between 350 kg/m$^3$ and 450 kg/m$^3$

DETAILED DESCRIPTION OF THE INVENTION

Non-limiting exemplary embodiments of the invention will now be described in greater detail with reference to the appended drawings in which.

MANUFACTURE ACCORDING TO PROCESS I

Figure 1:
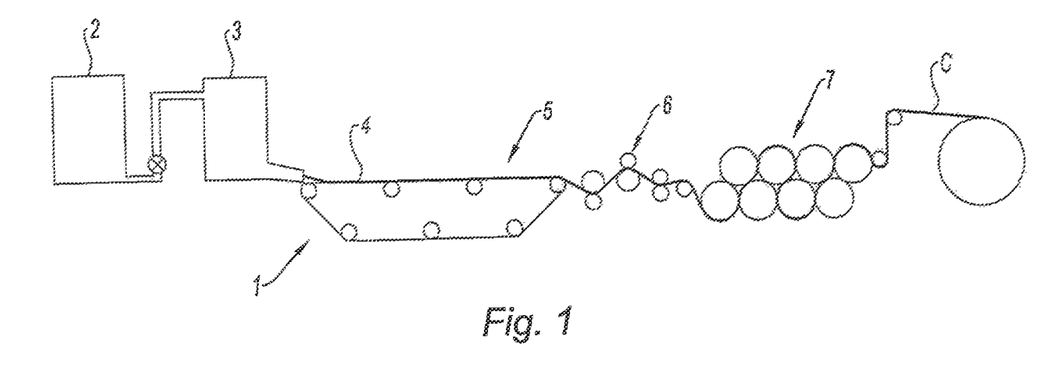
FIG. 1 shows a diagram of a paper machine seen in a side view used for the manufacture of a sheet of heavy paper according to process I suitable for the production of a core according to the invention.

Process I is implemented on a paper machine 1, which is itself conventional, as presented in FIG. 1. It is shown from the upstream end to the downstream end in the direction of manufacture. The pulp is contained in the chest 2 in which the fibres are kept in suspension and the additives are incorporated; the paper pulp is pumped into the head box 3, which in particular comprises a pulp distributor in the form of a blade, designated "jet" extending over the entire width of the machine. The pulp is deposited on the endless wire 4 of the forming table 5. This wire 4 forms a loop and runs endlessly around the parallel rollers of the table supporting it. It is jerked laterally so as to undergo a reciprocating motion that promotes uniform formation of the paper sheet and dewatering thereof. The fibres are aligned along the run direction of the wire. The paper sheet contains 75 to 85% water on leaving the table. The sheet is introduced into the press section 6 where the water content is reduced to 60 or 70%. The presses comprise several pairs of rubber-coated cylinders. This operation also increases the density of the sheet and improves its surface finish by mechanical action.

The paper sheet then enters the dry end, designated the drying section, of the paper machine, which comprises a plurality of dryers 7. The dryers 7 are cast iron drums heated internally with steam at a temperature high enough for the water contained in the sheet to be progressively evaporated until at least 90% dryness is achieved. Conventionally, the surface temperature of the drums is around 95° C. The sheet is held against the dryers by a heavy cotton felt or a drying fabric composed of cotton and artificial fibres.

The conventional machines for manufacturing printing or writing paper also include size presses, for surface treatment and for deposition of an appropriate composition, and optionally a breaker stack or calendering station before the paper is wound up into a reel. This reel is then used as master reel in the subsequent conversion steps.

In the present invention, the paper is essentially dried in the drying section before being reeled up.

To manufacture the sheet C of the invention, starch is added in the wet end of the paper machine before the press. Preferably, the starch is incorporated in the form of a suspension in water.

The starch may be deposited on the sheet by spraying, while said sheet is resting on the wire 4 as it travels along the forming table 5.

The starch may be introduced further upstream, prior to sheet formation. An advantageous zone for introducing it is located at the inlet of the transfer pump between the chest and the head box. Thus, the starch remains in suspension in the manufacturing composition introduced into the head box.

According to an important feature of process I of the invention, the starch introduced at this stage is not soluble in water, i.e. it is water-insoluble. It becomes soluble as the sheet passes through the drying section. The temperature of the successive dryers is advantageously regulated in such a way that the temperature of the sheet is gradually raised until reaching the gelatinization temperature of the starch that it contains. The temperature of the successive drums may be controlled between 60° C. and 100° C. The purpose is to maintain a sufficient amount of water in the sheet for gelatinization to effectively take place and to allow the starch to become soluble. If the amount of water were to be insufficient, some of the starch would not be gelatinized. Once the starch in the sheet has gelatinized and become soluble, said sheet can continue to be dried to the desired dryness.

The pressing, drying and reeling are adapted so as to obtain the desired final moisture content of the product.

The sheet thus continuously produced is reeled up for subsequent use.

The manufacturing parameters of the sheet C are determined so as to obtain a core having the desired properties.

The fibres used are long, short or recycled papermaking fibres and also mixtures thereof.

The water-insoluble starch is preferably chosen so that the size of the insoluble particles is large enough not to easily filter through the wet sheet.

It is also possible to incorporate other additives providing an additional function, such as disinfectants, cleaning agents or perfumes.

Retention agents may also be added so as to improve the retention of starch in the sheet, in particular for sheets of low weight.

Preferably, the starch is coloured so as to check that the binder is correctly distributed through the thickness. In addition, it represents an improvement in aesthetic terms.

Experimental Manufacturing Trial According to Process I on a Pilot Fourdrinier Paper Machine.

The machine comprised three dryer units each composed of two cylinders.

A 270 g/m² paper sheet containing about 33% starch was manufactured.

A pulp having a 2.5% concentration was prepared in a 10 m³ chest.

The pulp, having a mass of 250 kg, was made up of:

35% starch, i.e. 97.2 kg of starch; and 162.5 kg of fibres, one quarter being long fibres and three quarters being short fibres.

After mixing, the content of the mixing chest was transferred to the chest of the machine.

480 m of paper were manufactured.

The dryness was:

On leaving the Fourdrinier, between 16 and 17%;

On leaving the presses, 57%; and

At reel-up, 91%, for a dry weight of 243 g/m².

The temperatures of the six drying cylinders were controlled so as to have a progressive rise in temperature.

The starch content, which was measured in the sheet, was on average 33% relative to the total weight of the sheet.

A Manufacturing Example According to Process II is Now Described.

Figure 2:
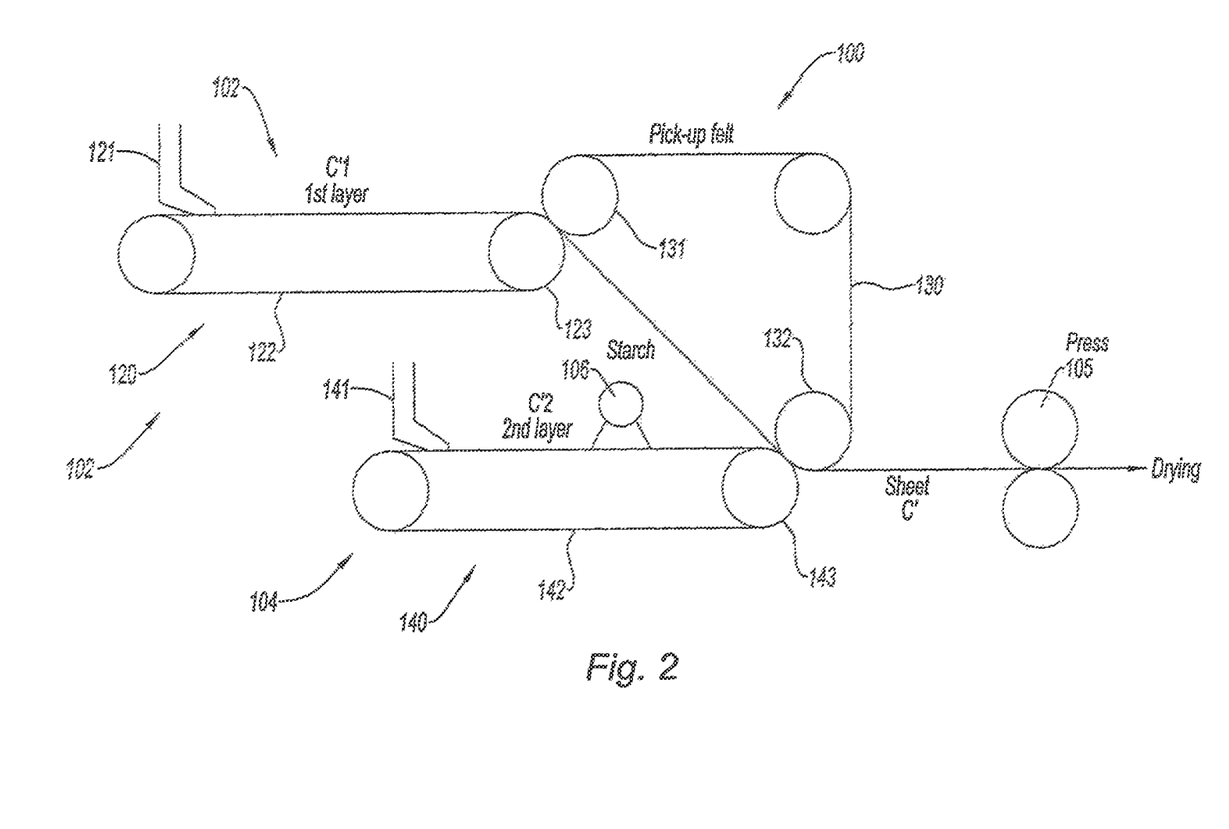
FIG. 2 shows a diagram of a paper machine seen in a side view used for the manufacture of a sheet of heavy paper according to process II.

According to the manufacturing example illustrated in FIG. 2, the paper machine 100 comprises a first unit 102 for forming a ply of papermaking fibres by wet processing on a Fourdrinier table, shown here, or else on a cylinder mould. The ply C'1 is formed by depositing, via the head box 121, a pulp formed from papermaking fibres suspended in water on the permeable moving wire 122 of the first forming table 120. The wire forms a loop and runs endlessly around the parallel rollers supporting it. The ply C'1 undergoes a first dewatering step as it travels along with the wire 122.

The first fibrous ply C'1 is taken up by a pick-up felt 130 which moves translationally in a loop around parallel support rollers, one 131 of which presses on the first ply C'1, which is partly dewatered, at the end of travel on the flat portion of the forming table 120 around the roller 123. The first ply C'1 is transported by the felt to a second Fourdrinier table 140 of the second unit 104 for forming a second ply C'2 of papermaking fibres. This ply C'2 is formed here, like the first, by depositing, via a head box 141, a pulp with a fibrous suspension on the moving wire 142 of the table 140. The fibrous ply C'2 thus formed is dewatered like the first one through the permeable wire. The pick-up felt presses via a roller 132 on the second fibrous ply C'2 so as to take off the second ply at the cylinder 143 at the end of the table 140. The two fibrous plies are joined together as a single sheet C' which is directed towards the gap left between two rollers of a press 105 for extracting a further portion of the water from the two plies while pressing the sheet. The sheet is then guided towards the drying unit (not shown), which may be conventional. In such an installation for manufacturing multiply sheets, the number of plies is not limited to two.

To manufacture the sheet C' of the invention, a system 106 for depositing starch L, in powder form, is placed upstream of the two cylinders 132 and 143. The system used enables the powder to be distributed uniformly in the desired amount over the width of the second fibrous ply C'2 and in a regular fashion in the run direction of the machine. Equipment comprising a product storage hopper, a product metering device and an oscillating brush is used to fulfil all these conditions. In industrial manufacture, the ply of papermaking fibres, here C'2, which is formed by wet processing and on which the starch is deposited, has a dryness ranging from about 10% to about 15%.

A powdered water-soluble starch is deposited on the second ply of papermaking fibres C'2—before the two plies are placed against each other and pressed together—when the ply is sufficiently dewatered and has a dryness sufficient to retain the product in the structure of the ply and to limit the removal of some of the starch with the dewatering water.

The deposited starch is sandwiched between the two plies thus formed, still in the wet state, and reacts with the residual water of each ply.

The fibre ply/starch/fibre ply complex is transported by the felt 130 to the pressing zone 105, the operating conditions of which are adapted, and then into the zone of the machine for drying the sheet.

It is possible to have other means for forming additional plies, whether or not associated with powder deposition means, so as to form a sheet that may comprise, for example, up to ten plies.

The sheet thus continuously produced is reeled up for subsequent use.

The manufacturing parameters of the sheet C' are determined so as to obtain a core having the desired properties.

The fibres used are long, short or recycled papermaking fibres and also mixtures thereof.

It is possible to incorporate other additives providing an additional function, such as disinfectants, cleaning agents or perfumes.

Preferably, the starch is coloured so as to check that the starch is correctly distributed on both sides. In addition, it represents an improvement in aesthetic terms.

The amount deposited is between 35 and 150 g/m$^2$.

The amount of starch in the sheet is therefore between about 10% and about 70% of the total mass of the sheet after drying.

The pressed fibrous sheet has a density between 450 kg/m$^3$ and 650 kg/m$^3$.

When dry water-soluble starch is incorporated, it has the advantage of using the water in the two plies to activate the starch. The pressing also ensures that the starch is correctly distributed through the mass of fibres.

Manufacture of the Core

The paper sheet was cut into narrow strips or strands that were then wound in a helix around a cylindrical former. An adhesive was applied to the overlapping parts of the turns so as to bond them together and form a rigid tube. Generally for the core of a roll of toilet paper, one or two strands are wound.

The technique for manufacturing the cores is known per se. It is adapted according to the nature of the binder in so far as it is necessary to take into account the rapid disintegrability of the strips by the adhesive used to join the strands together.

Tests

Core Compression, Disintegration and Down-toilet Discharge Tests Carried Out with a Sheet Obtained According to Process I The characteristics of a single-strand core A manufactured according to manufacturing process I were the following:
  weight of the sheet: 270 g/m$^2$;
  quality of the fibres: long fibre/short fibre mixture in the virgin pulp;
  starch reference: PERFECTACOTE A35 (modified water-insoluble starch) sold by the company Avebe;
  amount of starch retained by the finished sheet: 90 g/m$^2$, i.e. 33% of starch on the basis of the dry fibrous sheet;
  number of wall thicknesses of the cylinder: 1;
  weight of the wall of the cylinder: 270 g/m$^2$; and
  diameter and length of the cylinder forming the core: 40 mm and 97 mm respectively.

Core Compression Test:

The lateral compressive strength of the core was measured using the following method.

The core to be tested was firstly cut into a cylindrical portion bounded by two opposed faces, perpendicular to the axis of the cylinder, said portion having a length of 50 mm in a direction parallel to the axis.

This cylindrical portion was then positioned between the two metal plates of a testing machine, said plates being mutually parallel and initially separated by a distance slightly greater than the length of the cylindrical portion.

The cylindrical portion was placed so as to orient the axis of the cylinder along a direction perpendicular to the plane formed by one or other of the plates.

Said cylindrical portion was then compressed between the two plates, with measurements for a compression distance of 15 mm, at which the force in Newton was recorded.

Concomitantly, the resistance presented by the core was measured up to its maximum, i.e. just before the core was irreversibly destroyed.

Five measurements were taken each time and the average of the measurements was calculated.

The results are given in the table below together with those of a control core made of a one-strand cardboard also with a wall weight of 280 g/m$^2$.

|  | Weight | Mass | Lateral compressive strength |
|---|---|---|---|
| Cardboard control core | 280 g/m$^2$ | 3.9 g | 272.8 ± 9.6N |
| Tested core A | 270 g/m$^2$ | 3.6 g | 294 ± 12.5N |

This therefore shows that a core according to the invention containing 33% starch has a lateral strength at least equal to that of a conventional cardboard core.

Given that the principal stresses undergone by the core during its production/roll delivery cycle are essentially exerted on the edge, it may be considered that the core according to the invention completely meets the requirements therefore.

Core Disintegration Test:

The disintegration of the core A as manufactured above was measured in accordance with the NF Q34-020 standard.

The principle consisted in subjecting a specimen of the product to stirring in a certain volume of water. The time required for the specimen to disintegrate was measured.

This test was applied with the specimen of toilet-paper replaced with a specimen of the sheet according to the invention and a specimen of the cylinder forming the core according to the invention. More precisely, the specimen of the sheet was a specimen measuring 9 centimeters by 8 centimeters, i.e. an area of 72 cm$^2$, and the specimen of the core was a cylindrical specimen 5 centimeters in length.

The material, equipment and operating method are described in detail in the standard. It should be noted that complete disintegration corresponds to the moment when the pieces of the specimen move from the bottom of the beaker to the top of the stirrer, in other words when there are no longer large pieces beneath the impeller and when the dispersion of the pieces is uniform. At this time T, it is no longer possible to observe an appreciable change in state of the paper between the time T and the time T+5 seconds. The water used for this test was mains water.

It was observed that the specimen of the sheet according to the invention disintegrated very easily. Less than 15 seconds were required for the structure of the sheet to disintegrate and a fibrous suspension was obtained in less than 60 seconds.

The specimen of the cardboard control sheet having a weight of 280 g/m$^2$ only started to fall apart after 30 seconds, and the sheet was converted into pieces after 3 minutes.

Pieces with a size greater than 1 cm² still remained after 10 minutes.

It was also observed that the specimen of the core according to the invention formed from a single strip of 270 g/m² weight started to disintegrate in water more rapidly than a similar cardboard core obtained by winding a single cardboard strip having a weight of 280 g/m².

The term "similar core" should be understood to mean a core having approximately the same diameter and the same length as the core of the invention.

The specimen of the core according to the invention therefore disintegrated more rapidly than a similar cardboard core. This is because the specimen of the core according to the invention disintegrated in 10 to 15 seconds and a fibrous suspension was obtained in a time of less than 60 seconds.

The turns of the control core specimen opened up after about 60 seconds and the control specimen was in the state of large pieces after 7 minutes. After 10 minutes, pieces greater in size than 1 cm² still remained.

Moreover, again for comparison, it was observed in the Afnor NF Q34-020 test that the turns of a 400 g/m² two-strand cardboard core came unstuck after 60 seconds, the core only starting to disintegrate after 3 minutes. It disintegrated completely after 10 minutes, but cardboard pieces remained.

Core Discharge Test:

The discharge of the core in a domestic sanitary facility was checked based on the test method described in the guide published by EDANA (European Disposables & Nonwovens Association) for discharging wipes down toilets (FG 510.1 TIER 1 Toilet bowl & drainline clearance test).

The characteristics of the equipment, the test conditions and the test protocol are defined in this test method.

More precisely, two steps were studied in the application of this test to the cores:

1) discharge of the core down the toilet bowl: the core must disappear from the bowl after the flush has be actuated; and 2) elimination of the core from the drain line.

The equipment used for this test was a conventional toilet comprising a floor-standing bowl, a flushing mechanism, a water flush tank and a drain line. The drain line was a transparent plastic tube enabling the change in the products discharged down the bowl to be displayed. This line had a diameter of 100 millimeters and a length of 20 meters, and was installed with a slope of 2%.

The method consisted in introducing a series of ten cores into the bowl using the following procedure: a core was thrown into the bowl and then the flush actuated. The volume of this water flush was 5.5 litres. It was then checked whether the core had been discharged from the bowl and its position in the line was recorded. The operation was repeated with the ten cores, each time recording the position of the cores that were still in the line. Finally, complete removal of the core on leaving the line was noted.

The core according to the invention, namely a single-strand 270 g/m² core, was tested and passed the down-bowl discharge test and the removal-from-the-line test.

The similar 280 g/m² cardboard single-strand core did not even pass the down-bowl discharge test.

Compression and Disintegration Tests on the Core Made of a Sheet Obtained by Process II Cores were produced using process II.

The characteristics of the core manufactured were the following:

weight of each fibrous ply: 45 g/m2;
quality of the fibres: long-fibre/short-fibre mixture in the virgin pulp;
starch reference: AVEDEX from AVEBE;
amount of starch retained by the finished sheet: 90 g/m²; 50% starch;
number of fibrous plies: 2;
weight of the sheet: 180 g/m²;
number of thicknesses of the wall of the cylinder: 2; and
weight of the wall of the cylinder: 360 g/m².

A water-soluble starch was chosen so that it dissolved rapidly at high concentration.

Manufacture in the laboratory was carried out as follows:

Formation of a fibrous ply of 10% dryness, deposition of the ply on a wire, deposition of powdered starch, joining to another fibrous ply of 10% dryness, pressing by a roller for dewatering purposes and joining of the plies, take-off of the sheet thus formed and drying between two metal wires at 110° C.

A cylindrical core was then manufactured from two sheets formed as above.

The diameter and length of the cylinder forming the core were 40 mm and 97 mm.

Core Compression Test:

The compressive strength of the core in flat compression and in lateral compression was measured.

Five measurements were taken each time, and the average of the measurements was calculated.

The results are given in the table below, together with those of a control core made of a one-strand cardboard with a wall weight of 365 g/m².

|  | 15 mm flat compression | Lateral compression |
| --- | --- | --- |
| Cardboard control core | 5.64 ± 0.50 | 272.8 ± 9.6 |
| Core D with 30% starch | 6.15 ± 0.92 | 118 ± 25 |
| Core E with 50% starch | 12.11 ± 1.55 | 265 ± 41 |

Data Expressed in N

This table therefore shows that a core according to the invention containing 50% starch has a lateral strength similar to that of a cardboard core and that, in this case, the flat compressive strength is greater than that of a similar core made of cardboard. Above 65% starch, the sheet starts to become brittle and may no longer be suitable for manufacturing a core.

Given that the principal stresses undergone by the core during its production/roll delivery cycle are essentially exerted flat, it may be considered that the core according to the invention completely meets the requirements therefore.

Core Disintegration Test:

The disintegratability of the core as manufactured above was measured in accordance with the NF Q34-020 standard.

It was found that the core breaks up very easily, in less than 10 s. to destroy the structure, and that a fibrous suspension is obtained after about 30 s.

It was also observed that the core according to the invention starts to disintegrate in water more rapidly than a similar cardboard core obtained by winding a single strip of cardboard having a weight of 280 g/m².

The core according to the invention therefore disintegrates more rapidly than a similar cardboard core, formed from a single strip with a weight of 280 g/m², whether or not there is any stirring.

It can be observed that the papermaking fibres are coated with starch. The starch forms a network throughout the sheet that connects the fibres together in substitution for a part of hydrogen bonds. When the sheet is placed in contact with water, starch absorbs it and dissolves rapidly since the fibres are not bound by the starch they dissociate themselves very quickly. This would explain the rapidity with which the sheet loses its cohesion and disintegrate.

Comparative Tests Carried Out on Fibrous Sheets According to the Invention and Cardboard Sheets of the Same Weight.

A specimen measuring 15 mm in width by 152.4 mm in length is cut in the machine direction.

The specimen is fixed to a ring-shaped support (as described in the standard ISO 12192:2002), placed between two plates, and then subjected to a compressive force at a rate of 10 mm/min. The maximum resistance force is recorded.

For the measurement in the wet state, the specimen fixed in the support is dipped in water during a time less than 2 seconds. The measurement is carried out immediately after the dipping.

Specimens (E2 to E6) of sheets produced according to processes I and II were tested, as were also cardboard control specimens (E7 and E8) of substantially the same weight. The fibres used were virgin fibres.

The type and amount of starch in the specimens can be seen from the following table, where LF stands for long fibres and SF stands for short fibres:

| Reference | Process | Product | Fibres | Starch/content % | Basis Weight g/m² | Disintegration NF Q34-020 specimen of 8 × 9 cm² Time (s) | Table Test (3 ml in 6 s) Angle (°) | Ring crush test (N/15 mm) | | |
|---|---|---|---|---|---|---|---|---|---|---|
| | | | | | | | | Dry | Wet | w/d (%) |
| Intervention | II | Lab E2 | 75% LF/25% SF | Avedex 50% | 280 | 10 | 90 | >525 | 0.4 | <1 |
| | I | Lab E3 | 75% LF/25% SF | Perfect 50% | 285 | 10 | 90 | 400 ± 37 | 1.3 ± 0.2 | <1 |
| | I | E4 | 75% LF/25% SF | Perfect 32% | 280 | <10 | 90 | 419 ± 40 | 0.9 ± 0.4 | <1 |
| | I | Lab E5 | 100% SF | Perfect 28% | 290 | 12-15 | 90 | 480 to >525 | 0.8 ± 0.1 | <1 |
| | I | Pilot E6 | 100% SF | Stackote 14% | 288 | <10-15 | 90 | 448 ± 63 | 1.4 ± 0.3 | <1 |
| Standard board | | E7 | Recycle fibres | | 280 | >120 | 15 | 304 ± 29 | 21 ± 3 | 7 |
| | | E8 | Rec. fibres | | 280 | >120 | 15 | 273 ± 32 | 34 ± 3 | 12 |

Three tests were carried out: disintegration test; table test and ring crush test.

Disintegration Test

The disintegration test was made as described above. Compared with the NF Q34-020 standard, the test is carried out on a fibrous sheet or cardboard specimen measuring 8×9 cm², while applying a stirring speed of 400 revolutions per minute. The temperature of water is 20° C.

Table Test

This involves an internal test method for determining the loss of stiffness when the specimen is wetted.

A rectangular specimen measuring 2.54 cm in width by 13 cm in length is cut in the machine direction.

A table with a horizontal plane surface, a vertical plane and a straight edge at the intersection between the horizontal plane surface and the vertical plane is used. The specimen is laid flat on the table perpendicular to the edge. A portion of the specimen (10 cm) extends beyond the edge.

In the dry state, the specimen makes an angle of 0° with the plane.

The specimen is wetted using a motorized burette, the end-piece of which is placed 1 cm above the test piece: 3 ml of water supplied in 6 s. The water is deposited at the centre of the test piece above the edge, at the point where the specimen is going to make an angle with the horizontal plane.

On being wetted, the specimen is folded around the edge: the bend angle relative to the horizontal plane is recorded 6 seconds after the water has been delivered.

Ring Crush Test

The loss of wet strength of a specimen is determined by establishing the ratio of the lateral compressive strength in the wet state to that in the dry state.

With the processes described above, the following products can be obtained:

a fibrous sheet having a basis weight of between 20 and 1000 g/m² that disintegrates in water, comprising 10% to 70% starch on the basis of the total weight of the dry fibrous sheet,
  a. the disintegration time in water, measured in accordance with the NF Q34-020 standard applied to a specimen of the sheet of 9×8 cm², is less than 50 seconds, preferably less than 35 seconds, and more particularly less than 15 seconds,
  b. of which the loss of strength measured in accordance with the table test as reported in the specification corresponds to the loss of strength of a specimen of said sheet forming an angle of at least 85°, preferably between 88° and 90°, after having being wetted with water for a duration of 6 seconds.

a fibrous sheet having a basis weight of between 20 and 1000 g/m2 that disintegrates in water, comprising 10% to 70% starch on the basis of the total weight of the dry fibrous sheet,
  a. the disintegration time in water, measured in accordance with the NF Q34-020 standard applied to a specimen of the sheet of 9×8 cm², is less than 50 seconds, preferably less than 35 seconds and more particularly less than 15 seconds,
  b. the residual wet strength of which relative to its dry strength, as measured according to the ring crush test described in the specification, is less than 1%.

a fibrous sheet having a basis weight of between 20 and 1000 g/m² that disintegrates in water, comprising 10% to 70% starch on the basis of the total weight of the dry fibrous sheet, a. the disintegration time in water, measured in accordance with the NF Q34-020 standard applied to a specimen of the sheet of 9×8 cm$^2$, is less than 50 seconds, preferably less than 35 seconds and more particularly less than 15 seconds, b. the residual wet strength of which relative to its dry strength, as measured according to the ring crush test described in the specification, is less than 1%.

a fibrous sheet having a basis weight of between 20 and 1000 g/m$^2$ that disintegrates in water in less than 120 seconds comprising 10% to 70% starch on the basis of the total weight of the dry fibrous sheet, a. of which the loss of strength measured according to the table test as reported in the specification corresponds to the loss of strength of a specimen of said sheet forming an angle of at least 85°, preferably between 88° and 90°, after having being wetted with water for a duration of 6 seconds, b. the residual wet strength of which relative to its dry strength, as measured according to the ring crush test described in the specification, is less than 1%.

a fibrous sheet having a basis weight of between 20 and 1000 g/m$^2$ that disintegrates in water comprising, 10% to 70% starch on the basis of the total weight of the dry fibrous sheet, a. the disintegration time in water, measured in accordance with the NF Q34-020 standard applied to a specimen of the sheet of 9×8 cm$^2$, is less than 50 seconds, preferably less than 35 seconds and more particularly less than 15 seconds, b. of which the loss of strength measured according to the table test as reported in the specification corresponds to the loss of strength of a specimen of said sheet forming an angle of at least 85°, preferably between 88° and 90°, after having being wetted with water for a duration of 6 seconds, c. the residual wet strength of which relative to its dry strength, as measured according to the ring crush test described in the specification, is less than 1%.

According to the invention, the following products can be made out of any of the above mentioned sheets:

A core, consisting of a helical winding of one or more strips, having a fibrous sheet as described before.

A toilet paper roll comprising a core as described before.

A tampon applicator comprising a fibrous sheet as described before.

The invention claimed is:

1. A process for manufacturing a fibrous sheet comprising at least 30% of papermaking fibres, that disintegrates in less than 120 seconds in water, comprising:
suspending fibres in water;
forming at least a first fibrous ply and a second fibrous ply with said fibres:
depositing a starch on the second fibrous ply;
depositing the first fibrous ply on the second fibrous ply;
joining the two plies together as a fibrous sheet and drying the fibrous sheet, wherein the starch is deposited in a dry state on the second ply.

2. The process according to claim 1, wherein the starch is water-soluble.

3. The process according to claim 1, wherein the starch is water insoluble.

4. The process according to claim 1, wherein the deposited starch is a combination of a water-soluble and water-insoluble starch.

5. The process according to claim 1, wherein the starch is deposited in powder form.

6. The process according to claim 1, wherein at least a third fibrous ply is formed and deposited on said two plies with interposition or not of starch.

* * * * *